United States Patent [19]

Vick

[11] 4,267,830
[45] May 19, 1981

[54] COMBINATION SPINE BOARD AND HEAD STABILIZER

[76] Inventor: Wiley D. Vick, Stantonsburg, N.C. 27883

[21] Appl. No.: 6,471

[22] Filed: Jan. 25, 1979

[51] Int. Cl.³ .............................................. A61F 5/04
[52] U.S. Cl. ................................ 128/87 R; 128/87 B; 128/134
[58] Field of Search ................ 128/134, 84.2, 84 C, 128/87 R, 90, 87 B; 5/81, 82, 89

[56] References Cited

U.S. PATENT DOCUMENTS

| | | | |
|---|---|---|---|
| 3,218,103 | 11/1965 | Boyce | 128/134 |
| 3,449,776 | 6/1969 | Brock | 5/82 |
| 3,469,268 | 9/1969 | Phillips | 128/87 R |
| 3,650,523 | 3/1972 | Darby, Jr. | 128/134 |
| 3,672,364 | 6/1972 | Rankin | 128/134 |
| 3,724,453 | 4/1973 | Dixon et al. | 128/87 R |
| 3,732,863 | 5/1973 | Harrington | 128/84 C |
| 3,737,923 | 6/1973 | Prolo | 128/134 |
| 3,892,399 | 7/1975 | Cabansey | 128/134 |
| 4,156,424 | 5/1979 | Burgin | 128/341 |

*Primary Examiner*—Robert W. Michell
*Assistant Examiner*—C. W. Shedd
*Attorney, Agent, or Firm*—Mills & Coats

[57] ABSTRACT

In abstract a preferred embodiment of this invention is an improved spine board and head stabilizer system for transporting injured persons in a relatively stable position. The present invention provides for a short spine board that can be attached to both the back and the head of the patient while he is in a sitting position such as an injured party who remains in an upright position on the seat after an automobile accident. Once the patient is removed from the location of the accident, he can be placed on a full length spine board without disconnecting or otherwise loosening the head stabilizer of a short board. The quick engaging and releasing features of this invention are not only convenient to use but also greatly reduce the time required in properly strapping the injured party for removal and transport.

9 Claims, 9 Drawing Figures

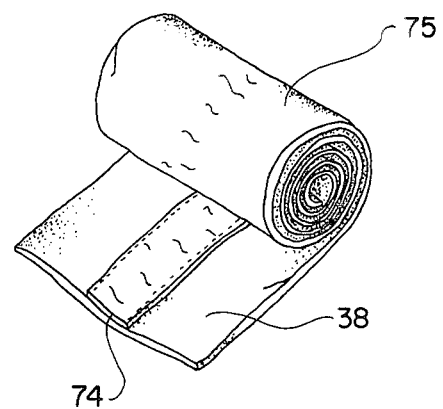
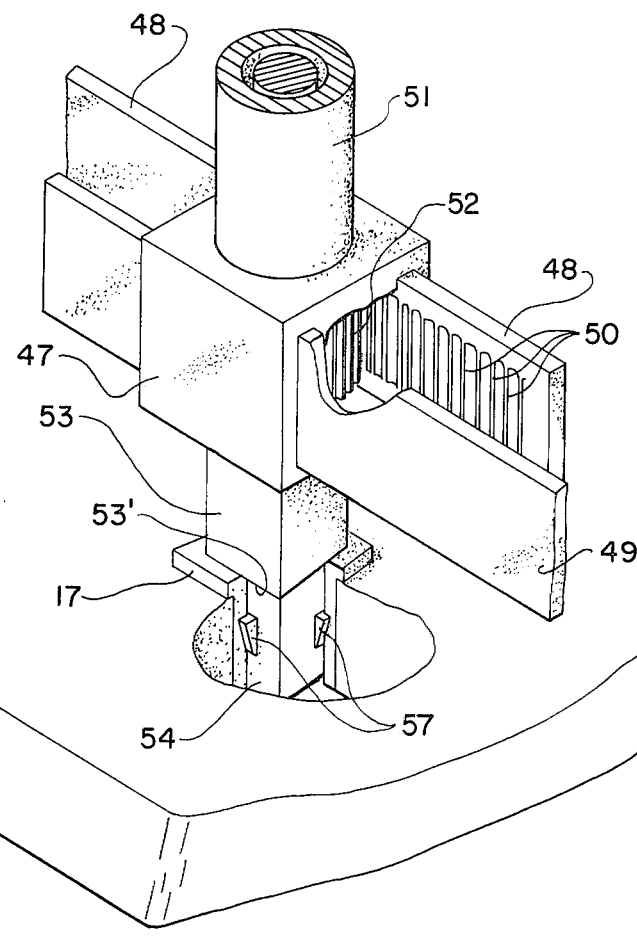

COMBINATION SPINE BOARD AND HEAD STABILIZER

FIELD OF INVENTION

This invention relates to medical appliances and more particularly to spine boards and related body and head stabilizing means for safe moval of patients with back and neck injuries.

BACKGROUND OF INVENTION

Elongated, flat, relatively stiff board like members, commonly referred to as spine boards, have been used over the years when it is necessary or desirable to move persons with broken, fractured or otherwise injured backs and/or necks. These patients have usually been in some manner strapped onto the board to restrict movement which could otherwise aggrevate or further injure the party. If a person has a broken or otherwise injured neck, sandbags placed on either side of the head have been used as stablizers to prevent undesirable and dangerous rolling of the head. These sandbags, while being much better than nothing, have their limitations in that it is next to impossible to place them tight enough against the head that all appreciable movement between them and the body is prevented. Also if the patient is being transported in an emergency or similar type vehicle, the danger of shifting sandbags is greatly increased thereby greatly increasing the danger of further injury to the patient.

Although short spine boards have been used to remove injured parties from confined areas such as when they are pinned in the wreckage of automobiles, airplanes and the like, the passing of straps around the patient and through openings in the board is a time consuming and laborious process and quite often must be accomplished under hazardous or even dangerous conditions where time is of the ultimate essence. Also means for stabilizing the head of the person strapped to the short board during initial removal has been inadequate at best.

Continuing to use the prior known procedures, once the patient has been removed from the confined area with the aid of the short board, he is laid down in a prone position and quite often is unstrapped from the short board and moved over to an adjacent full length spine board and is restrapped thereto, again usually by laboriously feeding the straps through openings in the board itself. If head stabilization is required, sandbags would be used as stabilizers on each side of the head and then transported to medical facilities or other remote locations are accomplished, hopefully with minimum additional injury occurring.

DESCRIPTION OF PREFERRED EMBODIMENT

After much research and study into the above-mentioned problems, the present invention has been developed to provide an improved spine board and head stabilizer for injured persons which allows such persons to be strapped to a short spine board for removal from a confined area and, if the neck of the person is broken or otherwise injured, the same can be stabilized prior to initial move. Once the patient has been removed from the confined area, he can be placed on a full length spine board which is simply placed under the short board with restrapping being accomplished without moving or otherwise disturbing the patient. Once the patient has arrived at the medical facility or other location, the head stabilizer as well as the body straps can be quickly and readily removed for transfer of the patient to a bed or other facility.

In addition to the above, the present invention is so designed that the patient, still strapped on the spine board with the head stabilizer engaged, can be placed on a x-ray table and the head stabilizer gently but simply pulled away from the head to allow x-rays to be made without in any way disturbing the patient. Also the body straps of the present invention are so designed that the various parts of the body of the patient can be x-rayed without removing or otherwise disturbing such straps.

Once the x-raying or similar processes are completed, the head stabilizer can be replaced and the patient removed, still on the spine board, to other medical facilities if deemed appropriate.

Since the head stabilizer portion of the present invention is removable from its associated spine board, it can readily be stored in a relatively compact compartment until needed, it does not take up any more room than sandbags, and it certainly is considerably more lightweight than such bags.

In view of the above, it is an object of the present invention to provide an improved spine board and head stabilizer wherein an injured person can be strapped to a short spine board with his head stabilized, can be transferred from a confined area to a more open area where a full length spine board can be connected to the short board, and the patient then transported to medical facilities or other appropriate location while still strapped to and stabilized by the original short board.

Another object of the present invention is to provide a removable head stabilizer for persons with neck injuries that is adjustable both transversely and longitudinally relative to the board on which it is mounted.

Another object of the present invention is to provide a head stabilizer for persons with neck injuries which is quickly attachable and detachable without disturbing the head of the patient.

Another object of the present invention is to provide a quick release means for connecting body straps to spine board.

Another object of the present invention is to provide a short spine board for removing injured persons from a confined area which is adapted to subsequently lie juxtaposed to and be interconnected with a long spine board for transporting patients to appropriate medical facilities.

Another object of the present invention is to provide a means for interlocking a short spine board juxtaposed to a long spine board to eliminate the necessity of transferring the patient who has required a short spine board to be removed from the confined area.

Another object of the present invention is to provide a push button quick release mechanism for attaching and releasing the body straps of a spine board.

Another object of the present invention is to provide a body strap for use in conjunction with a spine board wherein the tailing end is self-coiling.

Another object of the present invention is to provide a head stabilizer for a spine board wherein a shield is provided between the head of the patient and the operating mechanism of the stabilizer.

Another object of the present invention is to provide shoulder straps for use in conjunction with the head stabilizer of a short spine board wherein said straps are adjustable in a recessed adjustment means on the back side of the board.

Another object of the present invention is to provide a head stabilizer for use in conjunction with a spine board wherein head pads are mounted on ratchet arms to allow appropriate adjustment and yet can apply a firm holding grip.

Another object of the present invention is to provide a head stabilizer for use in conjunction with spine boards wherein the entire stabilizer can be removed by simply pressing a single release button.

Another object of the present invention is to secure a short spine board to a long spine board through use of a plurality of quick release strap attaching means.

Another object of the present invention is to provide a combination spine board and head stabilizer wherein, should a patient vomit due to his injuries, he can be rolled over to prevent suffocation while still firmly strapped to the board and stabilized by said head stabilizer without creating relative movement between body and head of said patient.

Other objects and advantages of the present invention will become apparent and obvious from a study of the following description and the accompanying drawings which are merely illustrative of such invention.

BRIEF DESCRIPTION OF DRAWINGS

FIG. 8 is a perspective view of the self-coiling strap portion of the present invention; and FIG. 9 is a fragmentary cutaway view of the ratchet arm portion of the head stabilizer of the present invention.

DETAILED DESCRIPTION OF INVENTION

Figure 1:
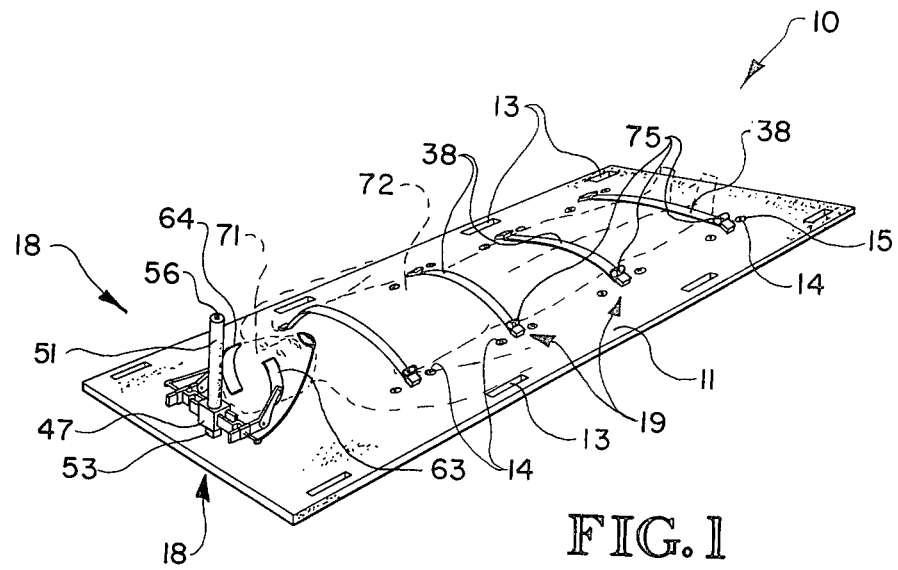
FIG. 1 is a perspective view of a full length or long spine board with the strap locks and head stabilizer of the present invention attached thereto.

With further reference to the drawings, the improved medical appliance of the present invention is indicated generally at 10. This appliance relates primarily to the transport of persons with back and/or neck injuries. Elongated board like members, commonly referred to as spine boards, have come into general use by hospitals, emergency medical personnel, rescue squads and the like. The present invention utilizes the concept of spine boards with considerable improvements therein to make them easier and more efficient to use as well as much quicker to operate which in many instances literally makes the difference between life and death of the patient.

The two basic types of known spine boards are used in conjunction with each other in the present invention, namely, a full length or long board 11 and a body trunk or short board 12.

The long board 11 includes standard handle or grip openings 13 and is generally the same size as the boards in common use today. Here the similarity between the prior known spine boards and the present invention ends.

A plurality of generally circular openings 14 are provided in the present invention. Each of these openings includes a metallic locking insert 15 whose purposes will become more apparent as hereinafter described in greater detail. The plurality of openings 14 are provided so that single board can be used for varying sized patients from the smallest, petitest woman to the largest, most robust man. In addition to openings 14 and their related locking inserts 15, at one end of spine board 11 are provided at least two centrally disposed, longitudinally aligned openings 16. These openings can either be square, rectangular or, as shown, trapezoid in shape but should not be round since the stabilization against twisting movement is absolutely necessary as will hereinafter be explained. Each of the openings 16 includes a locking insert 17 similar in function to locking inserts 15.

The head stabilizer indicated generally at 18 is adapted to mount in conjunction with openings 16 as will hereinafter be described.

Figure 3:
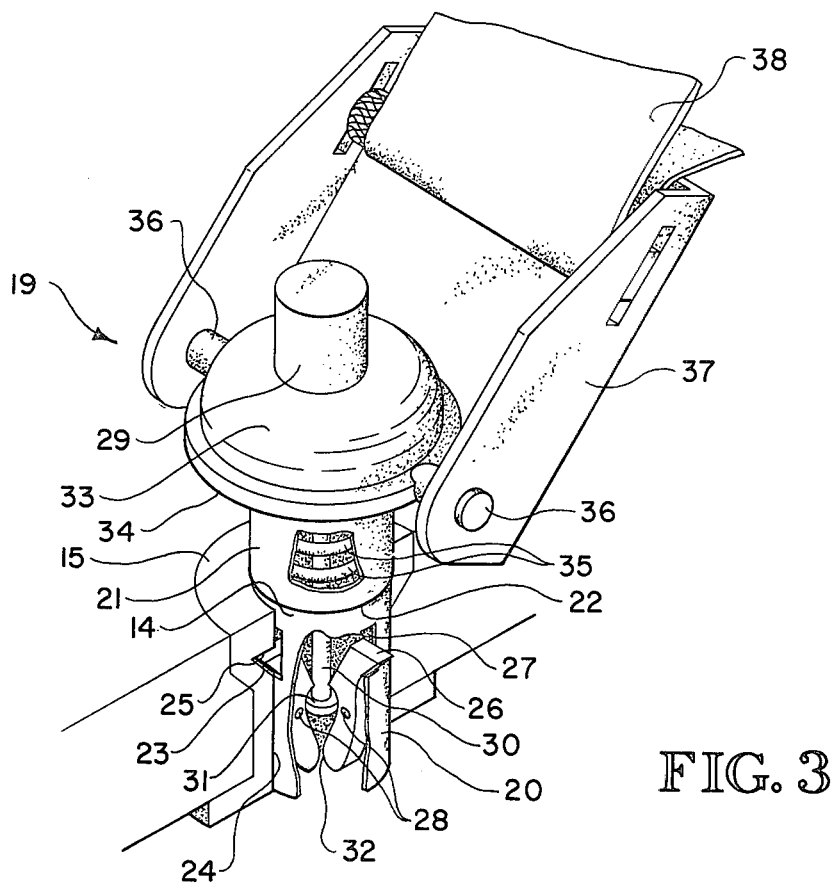
FIG. 3 is an enlarged cutaway perspective view of the strap locking mechanism of the present invention.

Referring more specifically to the strap locking mechanism indicated generally at 19 and shown particularly clear in FIG. 3, a hollow, generally cylindrical shaped insert portion 20 is provided. A collar portion 21 is provided immediately above the insert portion (as oriented in the drawings) and is of a slightly greater diameter than said insert portion thereby forming a shoulder 22. As the strap locking mechanism is inserted into opening 14 and its surrounding locking insert 15, should 22 engages the outer edge thereof as again seen clearly in FIG. 3. Since locking insert 15 is only slightly larger in interior diameter than insert portion 20, a snug but yet easily removable fit is accomplished.

A ring like groove 23 is provided on the interior wall 24 of locking insert 15. This groove has an upper portion or shoulder 25 which is adapted to lockingly engage cam locks or latches 26. Each of these latches is equally spaced about insert portion 20 and projects outwardly through openings 27.

As can be seen in the cutaway section of FIG. 3, each of the latches when in the engaged position rests against the insert housing 20 rather than riding on its pivot pin 28. This, of course, gives added strength to the locking mechanism of the present invention.

The pivot pins 28, of course, pivot the cam latches 26 so that when release button 29 is pushed downwardly, the shaft 30 connected thereto with its bulbous latch trip portion 31 will move downwardly engaging cam surface 32 to force cam latches 26 inwardly through openings 27 thereby releasing the engagement with shoulder 25 of locking insert 15.

Figure 7:
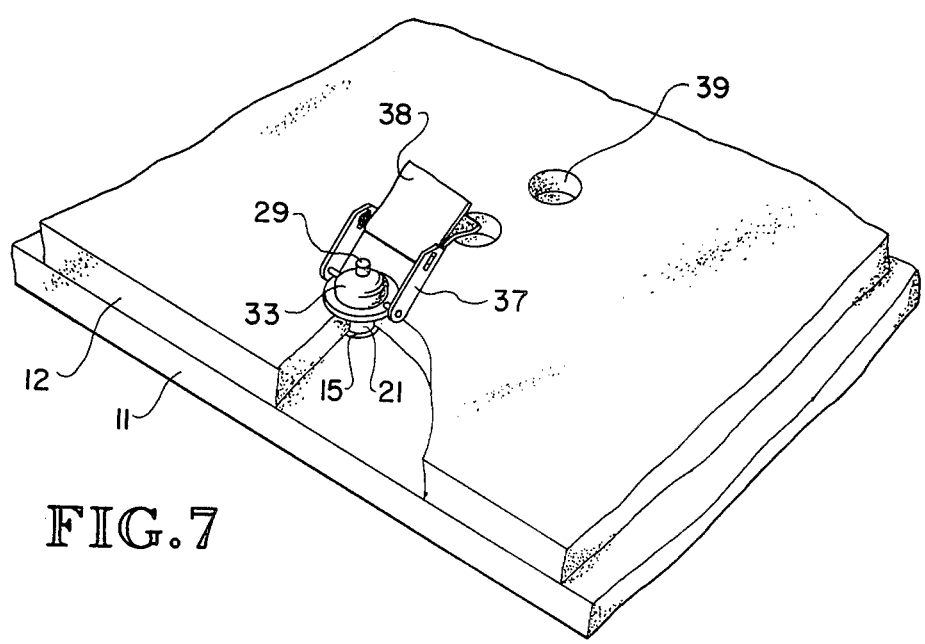
FIG. 7 is a cutaway perspective view of the strap locking means connecting a short and long board together.

Fixedly secured to collar portion 21 is housing cap 33. The lower portion of cap 33 is a generally flat planar surface 34 which is adapted to act as a shoulder juxtaposed to short board 12 when double boards are used as seen clearly in FIG. 7.

Within collar portion 21 and its associated housing cap 33 and disposed about shaft 30 is a biasing spring 35. This spring pushes upwardly on release button 29 thereby normally maintaining latch trip portion 31 in the position shown in FIG. 3 to maintain latches 26 in locking engagement with shoulder 25. The bias of spring 35 is of course, overcome by pressing downwardly on release button 29 to release locking mechanism 19 as hereinabove described.

Outwardly projecting from opposite sides of housing 33 are pivot shafts 36. These shafts are adapted to pivotably mount a more or less standard strap type buckle 37. This buckle is, of course, adapted to adjustably retain body strap 38 as will hereinafter be described in greater detail.

Although it is not specifically shown as such, the locking insert 15 can be produced as a two-piece unit and screwed or otherwise secured firmly into place to give the general overall configuration shown in FIG. 3.

Figure 5:
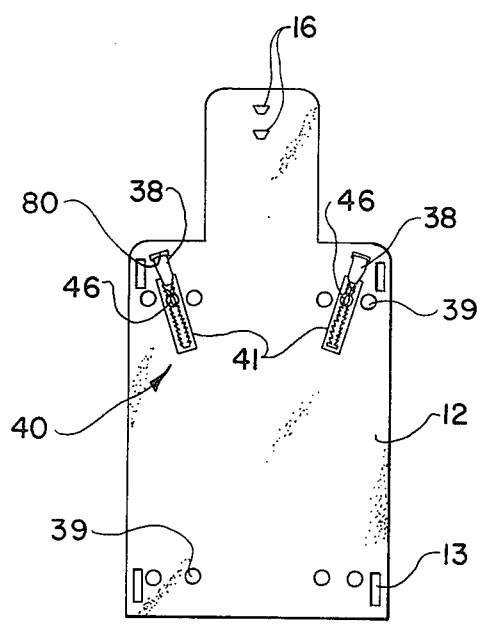
FIG. 5 is a rear elevational view of the short board showing the recessed shoulder strap adjusting means.

The short spine board 12 used in conjunction with the present invention includes a plurality of centrally disposed, longitudinally aligned head stabilizer openings 16 similar to those hereinabove described for long board 11. Also openings conforming in size and configuration to openings 14 of long board 11 are provided on the lower corners of short board 12 as oriented in the drawings. Additionally slightly larger, collar portion receiving openings 39 are provided in short board 12 as illustrated in FIG. 5. The function of these openings will be set forth hereinafter in greater detail.

Figure 6:
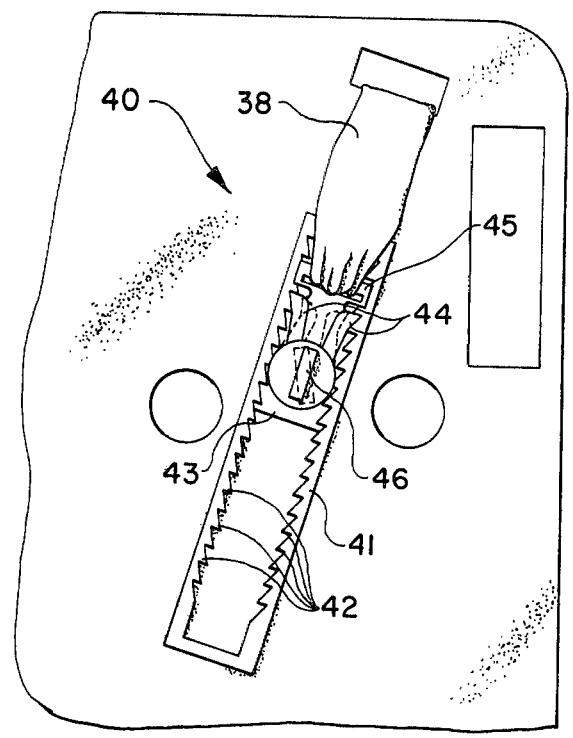
FIG. 6 is an enlarged view of the shoulder strap adjusting means.

Recessed into the back side (as used by a patient) of the short board 12 is a ratchet slide type shoulder strap adjusting means indicated generally at 40. As to details of adjustment means 40, a ratchet track 41 is provided with a plurality of teeth 42 thereon. A slide carriage 43 is adapted to move longitudinally back and forth beneath track 41. A pair of pawls 44 are provided which are pivotably mounted on carriage or slide 43. These pawls are biased outwardly toward the position shown in solid lines in FIG. 6 but can be deflected inwardly as shown in dotted lines. A strap loop 45 is fixedly secured to slide carriage 43. Thus as the slide carriage 43 is moved in the direction shown by the arrow in FIG. 6, the pawls 44 will slide over teeth 42 until reverse pressure is placed on the slide at which point the pawls will engage such teeth in a locking condition. To release the locked pawls from teeth 42, release button 46 is twisted as shown in dotted lines in FIG. 6 which, through a camming action (not shown but well known to those skilled in the art) pawls 44 will move to the position shown in dotted lines thus allowing slide 43 to move freely longitudinally along ratchet track 41.

Figure 2:
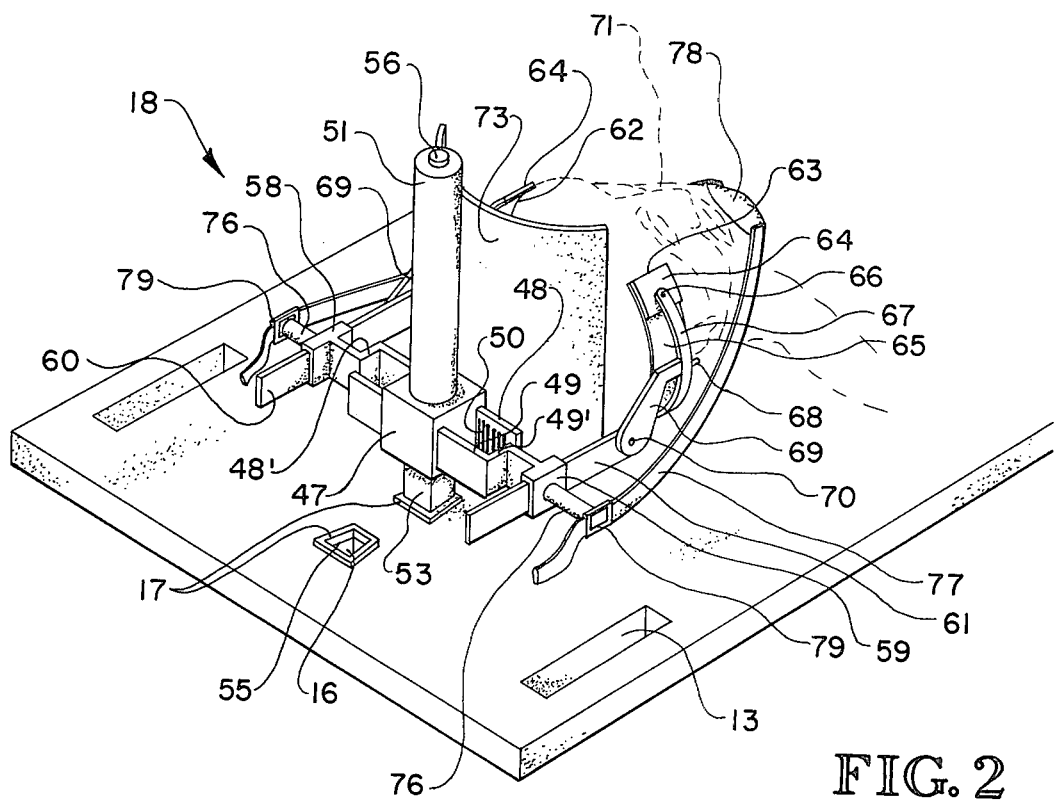
FIG. 2 is an enlarged perspective view of the head stabilizer portion of the present invention in operative position on a spine board.

Referring more specifically to the head stabilizer 18, a box shaped housing 47 is provided. A pair of opposed rack arms 48 and 49 are slidably mounted through said housing and can be seen clearly in FIGS. 1, 2 and 9. Each of these racks contain on facing surfaces teeth as are illustrated at 50. Upwardly projecting from housing 47 (as illustrated in the drawings) is handle 51. This handle is rotatively mounted relative to said housing and on its lower end has pinion 52 fixedly secured thereto for operative engagement with teeth 50 of racks 48 and 49.

Fixedly secured to and disposed below housing 47 is locking collar 53. This collar is adapted to engage the upper edge of locking insert 17 as collar portion 21 engages insert 15. An insert portion 54, corresponding to insert 20 of strap locking mechanism 19, is provided below collar 53 as disposed in the drawings. A locking groove 55 is provided about the interior of insert 17 which is similar to groove 23 of insert 15.

A release button 56 is provided on the top of handle 51 and extends downwardly therethrough into operative engagement with cam latches 57. The operation of latches 57 by manipulation of button 56 is the same as latches 26 operated by button 29 of strap locking mechanism 19 hereinabove described and further description of the same at this point would be considered redundant.

Offsets 48' and 49' are provided on one end of each of the racks 48 and 49, respectively. To the outermost ends of each of the offsets 48' and 49' are provided, respectively, friction sleeves 48 and 49. Generally parallelly disposed longitudinal support arms 60 and 61 are adapted to slidably mount through sleeves 58 and 59. As mentioned above, these sleeves are of the high friction coefficient type which allows the support arms to be slidingly moved therethrough but when sliding pressure is not being applied, the sleeve will hold the support arm relatively fixed. Friction means of this type are, of course, well known to those skilled in the art and further discussion of the same is not deemed necessary.

Head brackets 62 and 63 are composed of end portions 64 which are connected by resilient material such as fabric 65. Each of the end portions 64 are swivelly mounted at 66 to head bracket support 67. The central portion of support 67 is pivotably mounted at 68 to one end of bracket arm 69. The outer end of this arm is frictionally pivoted at 70 to the end of its respective support arm 60 or 61 as the case may be. Thus it can be seen that the height of head brackets 62 and 63 which grip the head 71 of the patient 72 can be adjusted by moving each of the bracket arms 69 relative to its longitudinal support arm and when the proper location has been obtained, the frictional pivot 70 will hold the same at that position.

While still referring to adjustment of the head stabilizer 18, handle 51 and its associated pinion 52 are also operated against a frictional drag or releasable unidirectional control means (not shown) so that once the gripping effect of the head brackets 62 and 63 on the head of the patient 71 is proper, handle 51 can be released and will remain relatively fixed thus effectively locking racks 48 and 49 relative to housing 47.

Disposed adjacent housing 47 and preferably secured thereto (although it could be separate therefrom) is protective shield 73. This shield not only protects the head of the patient from coming into contact with possible sharp edges of housing 47, but also prevents the hair of the patient from possibly becoming entangled in one of the racks 48 or 49 or other functional portions of the head stabilizer 18.

To retain head 71 of patient 72 from longitudinal movement, a chin strap 77 is provided which includes a chin engaging member 78 to maintain the strap in proper position. Buckles 79 adjustably engage the ends of strap 77 as seen clearly in FIG. 2. These buckles are, of course, mounted on the end of each of the shafts 76 which outwardly project from sleeves 78 and 79.

The use of straps 38 to hold the patient on the spine board creates a secondary problem in that these straps must be adequately long to take care of the largest possible patient and in so doing invariably a loose tailing end is the result. To prevent possible injuries from entanglement with these loose ends, they are usually in some manner tied to a portion of the board or its various parts. It is not only a time consuming process to tie the loose ends but it also requires additional time to undo the same when the patient is transferred from the spine board. Since quite often time is of the essence in moving a badly injured person, the tying up of loose strap ends becomes a problem of genuine concern.

Figure 4:
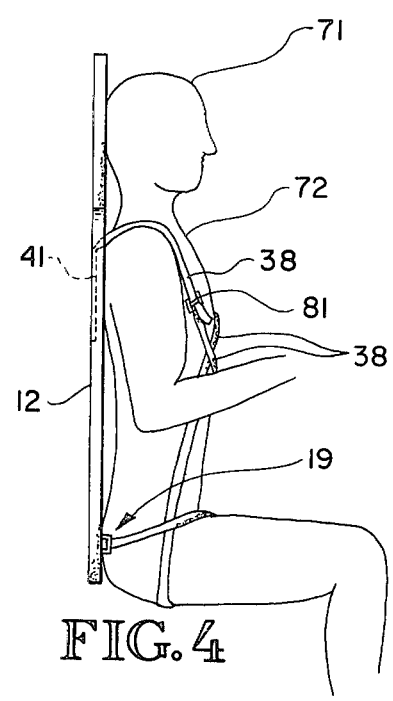
FIG. 4 is a side elevational view of the spine board of the present invention operatively attached to a patient in the sitting position.

The straps used in conjunction with the present invention are preferably of the type shown in FIG. 8. These straps include a plastic such as mylar or other similar type of material with a "memory" which, although it is deflected or unrolled, as soon as pressure is released from the same, it will immediately return to its original coiled position. This memory material 74 is sewn or otherwise secured to one side of strap 38 so that any excess tail beyond the buckle will automatically roll into a coiled condition similar to that shown at 75 in FIG. 8. Since the memory material 74 is flexible, it is a simple matter to unroll the coil 75 whenever it is necessary to manipulate the strap. In use of the medical appliance of the present invention, if the patient 72 is in a confined area, then the short board can be used. One end of strap 38' is, of course, secured to bracket 45 of adjustment means 40. Straps 38' pass through opening 80 of spine board 12 and terminate in buckle 81. Buckle 81 is adjustably secured to strap 38 which is crossed over the chest of the patient, is looped outwardly to inwardly around the leg of the patient, and is secured to strap locking mechanism 19 on the lower edge of board 12 as shown in FIG. 4. Since buckle 81 should not rest on certain tender parts of the body such as the collar bone or the breast of a woman, the location of buckle 81 is critical and the length of strap 38' must be varied from patient to patient. The shoulder strap adjusting means 40 allows this buckle adjustment to be quickly and efficiently accomplished by moving carriage 43 along ratchet track 41.

Once the patient 72 has been properly strapped onto board 12 and his head, if necessary stabilized, he can be removed from the confined area to a more open area. The patient 72 while still attached to spine board 12 is laid on his back with the full length spine board 11 located thereunder. The openings 39 of short board 12 are to be aligned with openings 15 of long board 11. Once the short and long boards are juxtaposed to each other with the openings therein properly aligned, the strap locking mechanism 19 shown in FIG. 4 are released and the legs of the patient moved from the sitting position of FIG. 4 to the prone position of FIG. 1.

Cross body straps 38 are then located across the chest, hips, knees and ankles of the patient and once the appropriate opening 15 has been selected, a strap locking mechanism 19 is simply inserted into such opening until latches 26 click into groove 23. The tailing end of strap 38 can then be snugged down and when the same is released it will automatically coil up as illustrated in FIG. 8. If a head stabilizer has been installed on the short board, the same can be left just as it is during transport of the patient to the hospital or other medical facility.

In considering the following description of the head stabilizer portion of the present invention, the observation should be made that the same can be used equally well with either the short board or the long board depending on whether the patient must first be removed from a relatively confined area or whether he can be immediately be placed on the long board.

Once the patient is properly disposed on the board on which he is to be moved, the appropriate opening 16 is selected depending on the size of the patient. The insert portion 57 of the stabilizer is then inserted into the selected opening until latches 57 connectingly engage groove 55. At this point, shoulder 53' of collar 53 should be in snug contactive engagement with insert 17.

With a counterclockwise twisting movement of handle 51, ratchet arms 48 and 49 are moved to their outermost position through the drive of pinion 52 within housing 47.

Next support arms 60 and 61 are longitudinally adjusted relative to the spine board until head brackets or pads 62 and 63 are appropriately located adjacent the sides of the head 71 of the patient.

Bracket arms 69 are then adjusted upwardly or downwardly as required relative to their respective support arms until the head pads are properly adjusted vertically adjacent the head of the patient.

Finally handle 51 is twisted in a clockwise direction which through the rack and pinion action of arms 48 and 49, will move pads 63 and 64 inwardly in snug gripping contact with the head of the patient.

Any variations in the contour of the head can be compensated for the pivot attachment 66 of the end portion 64 of each of the pads 62 and 63. The fabric interface 65 between ends 64, of course, allow such ends to swivel as necessary and yet give a broad surface contact.

Finally chin cup 78 is placed over the point of the chin of the patient and the ends of the chin straps 77 are tightened down by pulling the same through buckles 79.

From the above, it can be seen that when the head stabilizer portion of the present invention is so adjusted that pads 62 and 63 are in snug gripping contact with the sides of the head of the patient and such head is disposed adjacent shield 73 with the chin of the patient held tightly by chin strap 77, the patient's head will be held in relatively fixed position relative to the spine board. With the remainder of the body secured to such board by straps 38, transport of the patient can be accomplished without relative movement between such patient's body and head. By thus preventing such relative movement, further damage to broken vertebra, spinal cord or the like can be prevented.

The head and body stabilizing means of the present invention are in fact so effective that should the patient becomes sick and regurgitate, the entire spine board with the patient strapped thereon can be rolled 90 degrees to prevent the patient from drowning or otherwise choking and yet the relative relationship between body and head is rigidly maintained. This is not true with the older spine boards where, even though the patient is strapped to the same, the sandbags used to stabilize the head will slide when the board is tilted and thus the head has to be hand-held by one attendant while another rolls the board. This is a dangerous and far from efficient method which is only used in dire emergencies where death from choking is imminent. Thus it can be seen that the present invention has a great advantage in life saving situations.

Whenever the patient has arrived at an appropriate facility or it is otherwise desired to remove him from the spine board of the present invention, chin straps 77 are loosened and chin cup 78 removed without releasing or otherwise adjusting the head stabilizer, release button 76 can simply be pressed and the entire head stabilizing means 18 lifted from opening 16 and removed. In fact, because of the angle of chin strap 77 relative to the chin of the patient, if care is taken the stabilizer can be removed with the chain strap still in tight position by bringing the stabilizing means upwardly and over the forehead of the patient until chin cup 78 becomes loose and disengaged. In life saving situations where time is of the essence, this single feature of quick release of the head stabilizer can in many instances be very critical to the survival of the patient.

To release the body straps of the present invention, release button 29 is simply depressed to retract latches 26 from their retaining groove 23. The entire strap locking mechanism 19 can then be removed from opening 14. Again where time is of the essence in saving the life of the patient, the fact that the body straps can be immediately released by simply depressing a button rather than untying tailing ends and then releasing buckles can make the difference in life and death.

From the above, it can be seen that the present invention has the advantage of providing a short and long spine board which can be interconnected together by strap locking mechanisms without further securing means therebetween being necessary. A quickly connect and disconnect, easily adjustable head stabilizing means of superior stabilizing ability is also provided which can be used in conjunction with either a long or short spine board and does not have to be removed or otherwise adjusted when the patient is first placed on a short board and then on a long board. The present invention has the further advantage of providing a body securing means which is readily releasable when desired and yet contain a tremendous holding ability when in operative position.

The terms "upper", "lower", "top", "bottom", and so forth have been used herein merely for convenience to describe the medical appliance and its parts as oriented in the drawings. It is to be understood, however, that these terms are in no way limiting to the invention since the appliance may obviously be disposed in many different positions when in use.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. A combination spine board and head stabilizer comprising: a substantially planar, rigid short spine board having a top and bottom for use in conjunction with the head and trunk of a patient; a substantially planar, rigid long spine board having a top and bottom for use in conjunction with the head and entire body of the patient; mechanical means for removably connecting the bottom of said short board to the top of said long board in stacked juxtaposed relationship; and a mechanical head stabilizing means operatively mounted on the top of said short board for stabilizing the head of the patient using the board, said mechanical head stabilizing means includes a pair of head pads for grippingly holding opposite sides of the head, a pair of pinion driven rack means for laterally adjusting the relative position of said pads, a pair of support prongs longitudinally disposed relative to said board and adjustably mounted one on each end of said pair of racks for longitudinally adjusting the relative position of said pads, and means for vertically adjusting the relative position of said pads.

2. The medical appliance of claim 1 wherein the mechanical means for connecting said boards in juxtaposed relationship is a self- locking, releasable means.

3. The medical appliance of claim 2 wherein said mechanical, self-locking, releasable means is combined with a body strap securing means whereby the patient can be held in relative fixed position on said board.

4. The medical appliance of claim 3 wherein said body strap securing means is an adjustable strap buckle type means.

5. The medical appliance of claim 1 wherein said mechanical head stabilizing means is interchangeably usable with said short board and said long board separately to stabilize the head of the patient; the interchangeable mechanical means for stabilizing the head of the patient is a self-locking, readily releasable means.

6. The medical appliance of claim 1 wherein said pinion is driven by a rotatable handle.

7. The medical appliance of claim 1 wherein the means for vertically adjusting the relative height of said pads from said board are a pair of bracket arms pivotably mounted one on each of the longitudinally disposed support arms.

8. The medical appliance of claim 7 wherein said head pads are pivotably mounted one on the end of each of the bracket arms opposite their pivotable attachment to their respective support arm.

9. The medical appliance of claim 1 wherein a chin strap type retainer is provided for use in conjunction with the head stabilizer whereby further assurance of the prevention of relative movement between the head and body of the patient can be assured.

* * * * *